United States Patent [19]

Gould et al.

[11] Patent Number: 4,663,126

[45] Date of Patent: May 5, 1987

[54] POOL WATER TEST INSTRUMENT

[76] Inventors: Corby J. Gould, 2515 Nedson Ct., Mountain View, Calif. 94043; Carl R. Seago, 1012 10th Ave., Redwood City, Calif. 94063

[21] Appl. No.: 716,367

[22] Filed: Mar. 26, 1985

[51] Int. Cl.⁴ .................... G01N 1/12; G01N 31/22
[52] U.S. Cl. ........................................ 422/58; 422/61; 73/864.51
[58] Field of Search ............... 422/55, 58, 61, 68, 422/75, 236, 237; 436/163, 164, 165; 210/749, 169, 514; 73/863.31, 863.71, 863.85, 864.31, 864.32, 864.51, 864.52, 864.61, 864.64; 222/361, 362, 142.1, 142.2

[56] References Cited

U.S. PATENT DOCUMENTS

| | | | |
|---|---|---|---|
| 1,367,916 | 2/1921 | McKeig | 222/361 |
| 2,059,608 | 7/1932 | Rochester | 222/361 |
| 3,169,834 | 4/1962 | Otto et al. | 422/68 |
| 3,276,637 | 10/1966 | Fender | 222/361 |
| 3,692,490 | 10/1970 | Hall | 422/68 |
| 3,701,633 | 10/1972 | Davis | 436/163 |
| 3,768,974 | 10/1973 | Storm | 422/58 |
| 3,910,764 | 10/1975 | Tower | 422/61 |
| 4,235,839 | 11/1980 | Vesterberg | 73/864.51 |
| 4,454,775 | 6/1984 | Ellis | 422/55 |
| 4,515,023 | 5/1985 | Kershner | 73/864.51 |

FOREIGN PATENT DOCUMENTS 1556082 11/1979 United Kingdom ............. 422/68

Primary Examiner—Barry S. Richman
Assistant Examiner—Johnston
Attorney, Agent, or Firm—Cushman, Darby & Cushman

[57] ABSTRACT

A portable, hand-held instrument is provided for capturing a predetermined volume of water to be tested and transferring a measured quantity of reagent into the water for making a visual test of a water condition. A slide is included which has a measuring chamber having a size defining a predetermined volume of reagent. This slide is shiftable from a loading position in which water may be introduced into a mixing chamber and reagent from a supply chamber fills the measuring chamber, to a mixing position where the measuring chamber is isolated from the reagent supply chamber but is in communication with the mixing chamber for mixing the reagent with the water sample. Ports existing in the side of the instrument allow for the introduction of the sample water. Doors are attached to the slide which leave these ports uncovered when the slide is in the loading position and which cover them when in the mixing position.

9 Claims, 8 Drawing Figures

POOL WATER TEST INSTRUMENT

BACKGROUND OF THE INVENTION

This invention pertains to devices for testing pool water conditions, and more particularly, to such an instrument which automatically measures a predetermined volume of reagent and transfers it to the water sample.

In order to maintain a contained pool of water, as would be found in a swimming pool, hot tub or spa pool, in a desired condition, it is necessary to measure certain conditions of the water. During measurement of a particular condition, a predetermined volume of a reagent or indicator solution is added to a predetermined volume of sampled water. Most commonly, the pH and chlorine levels are determined. The test reagents now generally used are orthotolidine for testing chlorine and phenol red for pH level. Orthotolidine, when added to water containing chlorine, turns the water various colors of yellow depending on the concentration of chlorine in the water. Similarly, the addition of phenol red to the water sample turns the sample various shades of red depending on the pH of the water. The importance of proper pH and chlorine balance are well-known in the trade.

Typical simplified portable test kits provide a pair of clear vials mounted in a holder next to color charts which show the various concentration levels of a specified water condition. The two vials are submerged in a pool of water to fill them to a desired level. Then, a specified number of drops of appropriate reagents are dispensed into the water samples. The resulting water color is compared with the associated charts to determine the condition of the pool water. Changes may then be made in the water condition to bring it to a desired level. Although these kits have very simple structure and are inexpensive to make, they do not provide consistent measurement results because the drop sizes vary.

More involved apparatus have also been developed in an attempt to improve the reliability of the testing process. These devices typically are rather complex and have several different moving parts. One such instrument is shown in U.S. Pat. No. 3,692,490 to Hall. The instrument is submerged in a pool and a pair of concentric-shafted T-handles are brought together to draw sample pool water into a reservoir created by the shifting of the handles. A sample of reagent is simultaneously forced through a one-way valve from a reagent reservoir into the water reservoir. Venting of the reagent chambers is provided through the shaft of one of the handles, the top of which must be maintained above water level. Further, an entry port which allows entry of the sample water is made small, so that water will not drain out of it when the instrument is held out of the water for observing the resulting color of the water. Further, there is involved valving provided to assure that reagent rather than water is replaced in a plunger cylinder forming part of the reagent supply cylinder during a water-ejecting phase after the test has been performed. The complex structure of these devices makes them more expensive to produce and are subject to operational malfunction.

Another, more simple, device is disclosed in U.S. Pat. No. 3,910,764 issued to Tower which shows a handheld device containing a spring biased slide to cover a water sample reservoir and a spring biased one-way valve injection plunger for drawing water from a reagent reservoir and forcing it into the water chamber. A special dimple is provided in the slide which covers the water chamber to accommodate the increased volume provided by the injection of the reagent. In this device there is no vent to allow the reagent supply chamber to accommodate the withdrawal of reagent from it during testing. Further, the accuracy of reagent supply injected into a water sample will vary depending upon the amount of reagent which remains in a conduit housing a spring and valve through which the dispensed reagent must pass. Although fairly simple to use, the various springs and valving make it relatively expensive to produce.

Fixed position liquid testing instruments have been developed which, besides not being handheld or portable, rely on a pressurized flow of water through them for operation. One such instrument is disclosed in U.S. Pat. No. 3,169,834 issued to Otto et al. which is used with a pressurized supply of a liquid to be tested. It provides an involved channeling scheme which is used to fill a mixing chamber during a testing procedure, to bypass that mixing chamber when it has been filled, and to flush it after a test has been completed. It includes a plunger which transfers a metered amount of reagent into an upstream channel where it is washed down into a mixing chamber having a drain. A plunger which transfers the reagent also closes the drain. If the movement of the plunger to the drain-closing position is not done quickly enough, some reagent may easily be washed out of the mixing chamber before a measurement can be made. This instrument is not usable in a contained pool test environment where a pressure supply system is not readily available. Further, it is not portable for transportation to a pool to obtain a water sample and then removal therefrom so that it does not interfere with the pool environment between testing operations.

The present invention provides a simplified portable hand-held, pool-water test instrument for transferring a predetermined volume of a reagent into a predetermined volume of water obtained from a contained pool. Means are included for providing a supply of reagent and for holding a predetermined volume of water which is spaced from the reagent supply. Means are also included for introducing sample water into the instrument and for transferring reagent from the reagent supply into the sample water. The reagent transferring is preferably provided by means defining a measuring chamber which is shiftable between a loading position where it is fillable with a predetermined volume of reagent and a mixing position where it is mixable with the sample water.

The preferred embodiment of the invention includes a reagent supply chamber which is sealable from the atmosphere and a separate mixing chamber capable of holding sample water. A slide disposed below the reagent chamber has the measuring chamber which is positionable in communication with the reagent supply chamber for filling with reagent. The slide is then shifted to the mixing position where the measuring chamber is open to the mixing chamber. Sample water is introduced into the mixing chamber through external ports which are sealable from the atmosphere by doors joined with the slide. The doors are shifted into positions covering the ports as the slide is shifted to the mixing position.

This invention provides a self-venting instrument which may be used repeatedly so long as sufficient reagent supply exists. Further, it provides for simplified operation in that only a single slide moves during operation of the instrument. Further, no valves are used since reagent is transferred by a simple slide movement. These and additional features and advantages of the present invention will be more clearly understood from a consideration of the drawings and the following detailed description of the preferred embodiment.

BRIEF DESCRIPTION OF THE DRAWINGS

The reference to the accompanying three sheets of drawings.

DETAILED DESCRIPTION OF A PREFERRED EMBODIMENT

Figure 1:
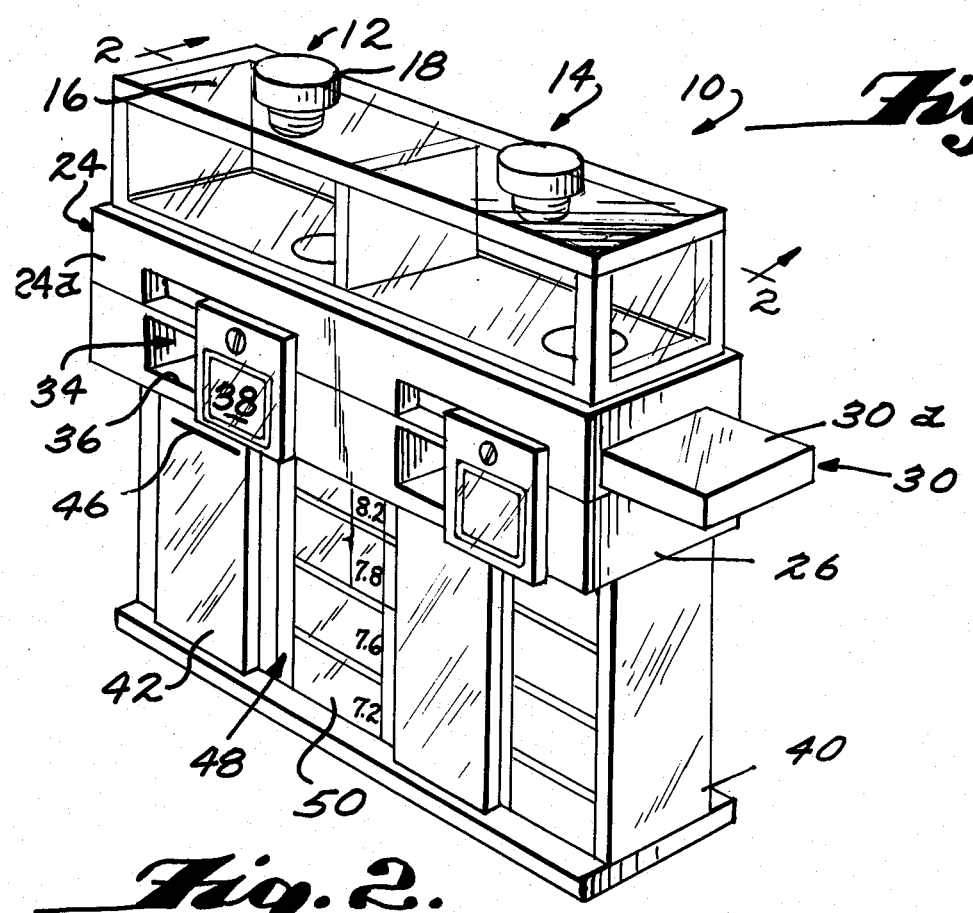
FIG. 1 is a perspective view of a pool water test instrument made according to the present invention.
Figure 2:
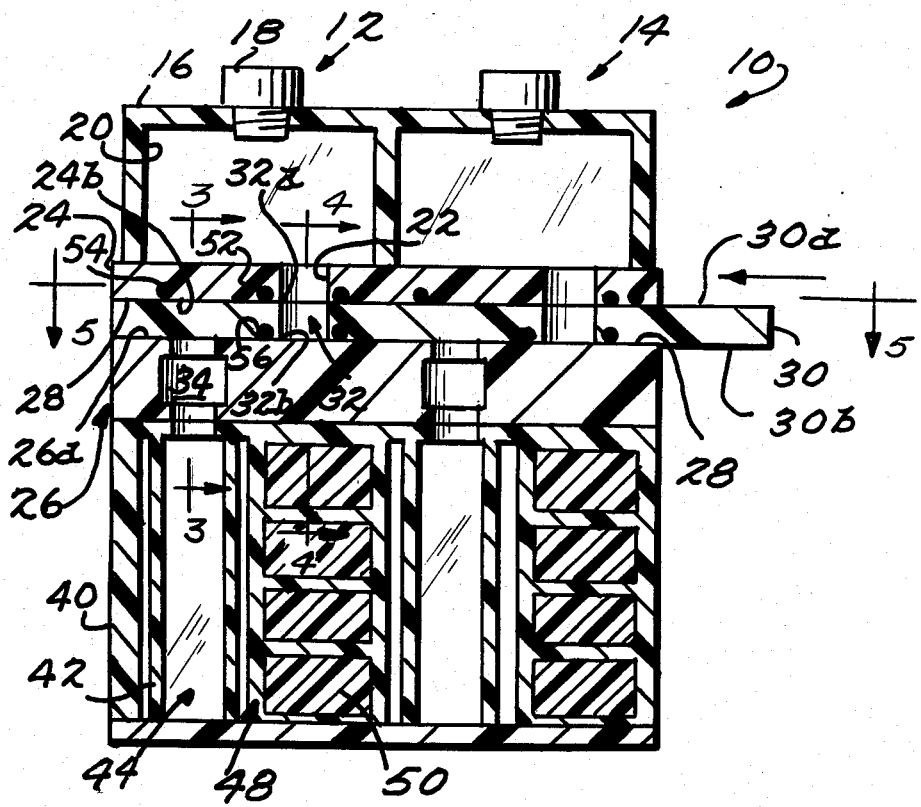
FIG. 2 is a cross-sectional view taken along line 2—2 in FIG. 1.

Referring initially to FIGS. 1 and 2, a portable handheld pool water test instrument, shown generally at 10, includes a pH testing instrument portion, shown generally at 12, and a chlorine concentration testing portion, shown generally at 14. Except for visual indicating charts and the size of a reagent measuring chamber, these two portions are substantially identical. Only the left or pH-measuring portion will be described with the understanding that the statements will also correspond to the chlorine portion.

Means are included for providing a supply of reagent. More particularly, disposed at the top of portion 12 is a reagent supply container 16 having an inlet on the top of it in which is removably disposed a sealing cap 18. Contained within container 16 is a reagent supply chamber 20 which holds a supply of a reagent for use in several water sample tests. Container 16 is preferably made of a clear plastic so that the level of the contents may be viewed externally. Disposed in the bottom of chamber 20 is a drain 22 which extends through what will be referred to as a guide plate 24.

Means are provided for transferring reagent from chamber 20. This includes plate 24 which has legs disposed along its sides and at its corners, such as leg 24a, which are attached to a channel base plate 26 which has a substantially planar top surface 26a. Guide plate 24, interposed legs 24a, has a downward facing surface 24b which also is generally planar and parallel with base plate top surface 26a. Surfaces 24b and 26a as well as the inwardly facing edges of legs 24a form what is referred to as means defining a channel 28.

Figure 3:
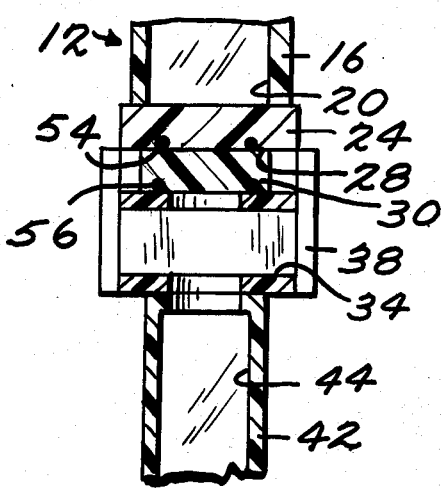
FIG. 3 is a fragmentary cross-sectional view taken along line 3—3 in FIG. 2.

As is also shown in FIGS. 2, 3, disposed for snug, mating and sliding receipt within channel 28 is a slide 30. Slide 30 generally has a rectangular cross-section and has an upper surface 30a which conforms with guide plate surface 24b and a lower surface 30b which conforms with base plate top surface 26a. The guide plate legs restrain the slide from lateral movement.

Figure 4:
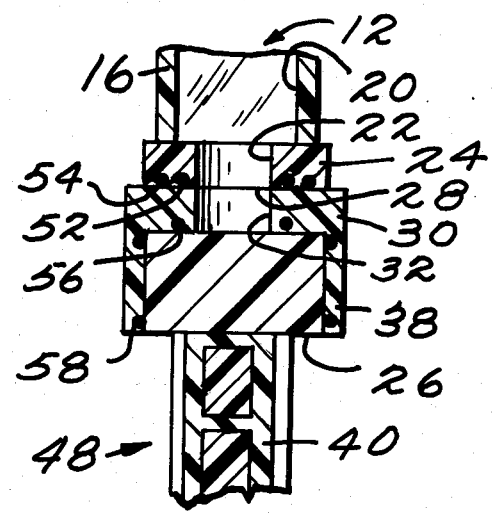
FIG. 4 is a fragmentary cross-sectional view taken along line 4—4 in FIG. 2.

As will be seen, slide 30 is shiftable from the position shown in FIGS. 1, 2, which is referred to as a loading position, to another position to the left in the figures referred to as a mixing position. Included in the means for transferring reagent is means defining a measuring chamber 32. Specifically, slide 30 includes a measuring chamber 32 which extends through it from an upper opening 32a disposed in upper surface 30a downward to a lower opening 32b disposed in lower surface 30b. When slide 30 is in the loading position, as is particulary shown in FIGS. 2, 4, measuring chamber 32 is in communication with drain 22, and therefore supply chamber 20.

Means are included for holding water. That is, in part, with instrument 10 in an upright position as shown, base plate 26 has disposed within it a passageway 34 which extends vertically through it. Means are also provided for introducing water into passageway 34. This is specifically provided by ports, such as side port 36 shown in FIG. 1, which communicate passageway 34 with the exterior of instrument 10. Means are also provided for preventing water from being introduced through the side ports. This is provided by doors, such as door 38, integrally formed with slide 30 which shift from the positions shown when slide 30 is in the loading position to positions covering ports 36 when the slide is in the mixing position.

A base frame 40 is disposed below and supports base plate 26. The means for holding water is further provided by a vial 42 made of clear plastic mounted on frame 40. Vial 42 is open at its upper end to communicate with passageway 34. Passageway 34 and vial 42 form what is referred to as a mixing chamber. Vial 42 forms a lower portion of the mixing chamber, which portion is sized to hold the predetermined volumes of water and reagent. An index line 46 is preferably marked at an appropriate level on vial 42 to indicate visually the predetermined volume of water. Passageway 34 then forms the upper portion of mixing chamber 44. When slide 30 is in the mixing position, measuring chamber 32 is disposed above and in communication with passageway 34 and is isolated from drain 22.

Disposed next to vial 42 is a color indicating chart, shown generally at 48. Chart 48 includes a plurality of panels, such as panel 50, which have colors and numerical indexes corresponding to varying degrees of concentration of the particular water characteristic being measured. These charts are in general use in the industry and will not be described further.

Figure 5:
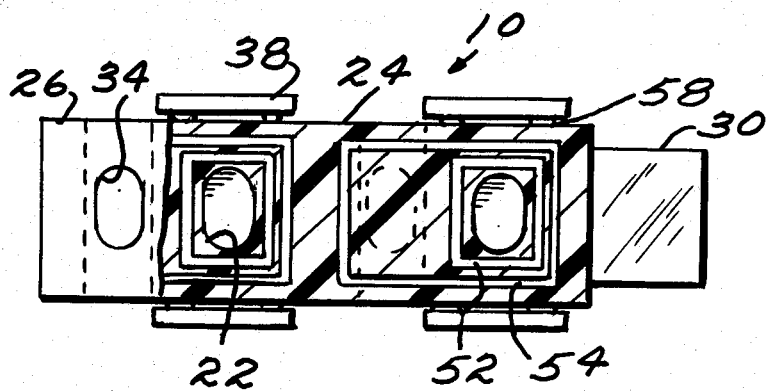
FIG. 5 is a partially broken away cross-sectional view taken along line 5—5 in FIG. 2.

Various means are provided for sealing measuring chamber 32 from other portions of instrument 10. In this preferred embodiment, a first sealing means is provided in the form of an O-ring 52, as shown particularly in FIG. 5, which extends around the perimeter of upper opening 32a. This O-ring is interposed slide 30 and channel 28 and is held in position by a corresponding groove in guide plate 24. It seals the junction between drain 22 and chamber 32 when the slide is in the loading position. When slide 30 is in other positions, it seals drain 22 from channel 28. A second sealing means is provided in the form of a larger O-ring 54 extending coplanarly and is around O-ring 52. Specifically, it is disposed in guide plate 24, as is O-ring 52. It seals upper opening 32a of the measuring chamber in its various positions from channel 28 generally. Specifically, it extends around the path of opening 32a as it travels between the two terminal positions of slide 30. Thus, when slide 30 is in the mixing position, chamber 34 is sealed from the balance of channel 28 as well as from drain 22 (by O-ring 52).

Means are also provided for sealing the lower opening 32b from the portion of channel 28 surrounding it. That is, another O-ring 56 is disposed in the lower surface of slide 30 surrounding opening 32b. Thus, when slide 30 is in the mixing position, O-ring 56 seals the junction between measuring chamber 32 and channel 28. When it is in the loading position measuring chamber 32 is sealed from passageway 34.

Means are provided in the preferred embodiment for preventing the introduction of water into mixing chamber 44 when slide 30 is in the mixing position. This is provided specifically by an O-ring 58, attached to door 38, interposed door 38 and channel base plate 26. O-ring 58 seals port 36 when the slide is in the mixing position.

Figure 6A:
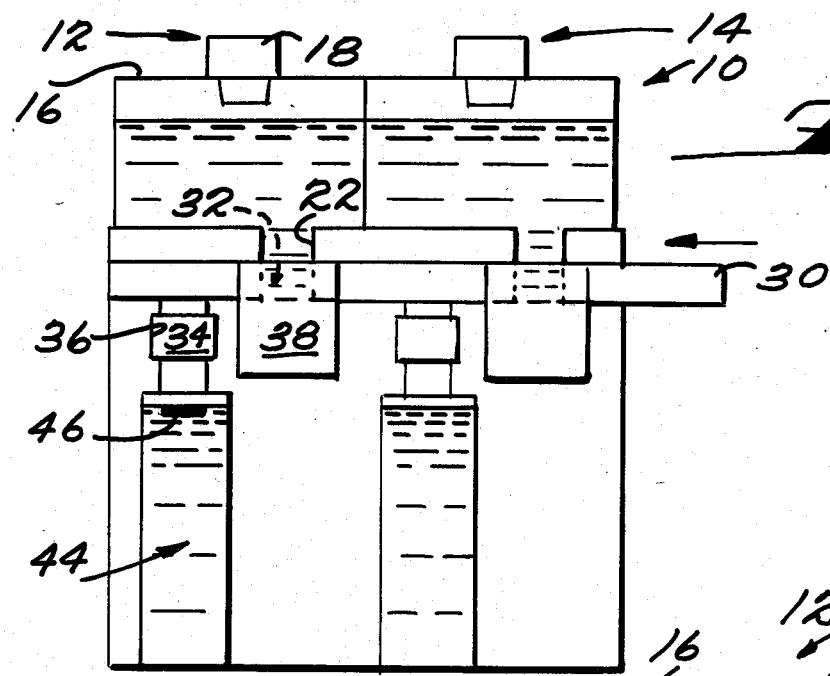
FIGS. 6a–6c are simplified schematics illustrating operation of the instrument of FIG. 1 as viewed from the exposed side in that figure.
Figure 6B:
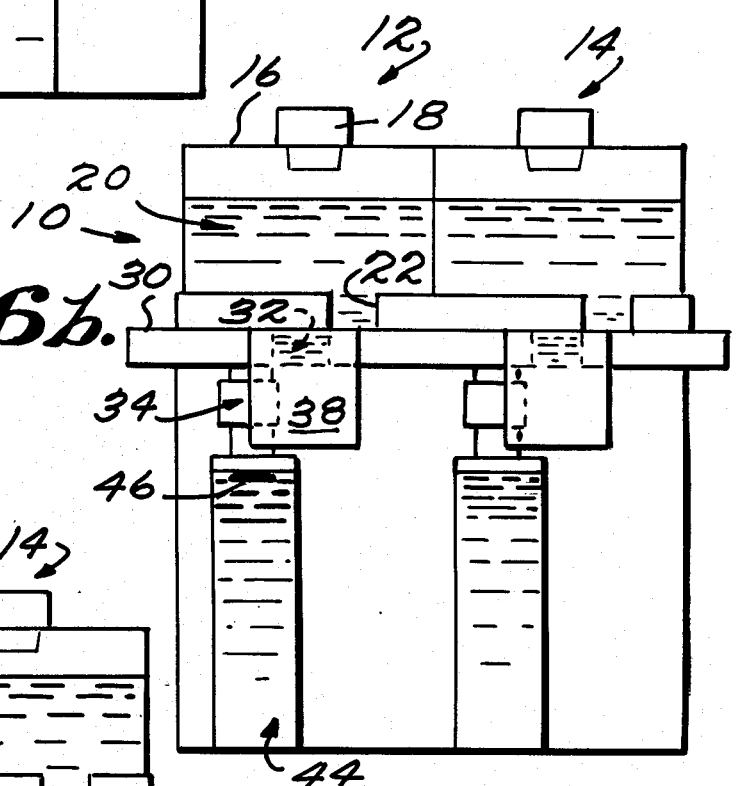

The operation of instrument 10 will now be described with particular reference to FIGS. 6a-6c. Referring initially to FIG. 6a, a supply of a desired reagent is first placed into supply chamber 20 with sufficient quantity to perform several tests. Slide 30 is then placed so that measuring chamber 32 is in communication with drain 22, and therefore supply chamber 20, as shown. Measuring chamber 32 becomes the lowest portion of the total supply of reagent with the slide in this position. Any atmospheric gas previously existing in chamber 32 rises to the top of the reagent supply, being replaced by reagent. It can be seen, with slide 30 in the loading position, door 38 is shifted away from port 36, leaving open communication between the exterior of instrument 10 and mixing chamber 44.

With cap 18 sealing the inlet of container 16, and slide 30 held in the loading position, instrument 10 is submerged in a pool of water which it is desired to test with the instrument in an upright position. Air contained in vial 42 is replaced by pool water. Instrument 10 is removed from the pool and tilted so that water which extends above index line 46 may be poured off to reach the desired predetermined volume of water for testing.

With a predetermined volume of reagent captured in measuring chamber 32, slide 30 is shifted toward the mixing position. FIG. 6b shows the slide in an intermediate position with measuring chamber 32 disposed between and isolated from drain 22 and passageway 34. This isolation is important so that there is never any direct communication between supply chamber 20 and mixing chamber 44.

Figure 6C:
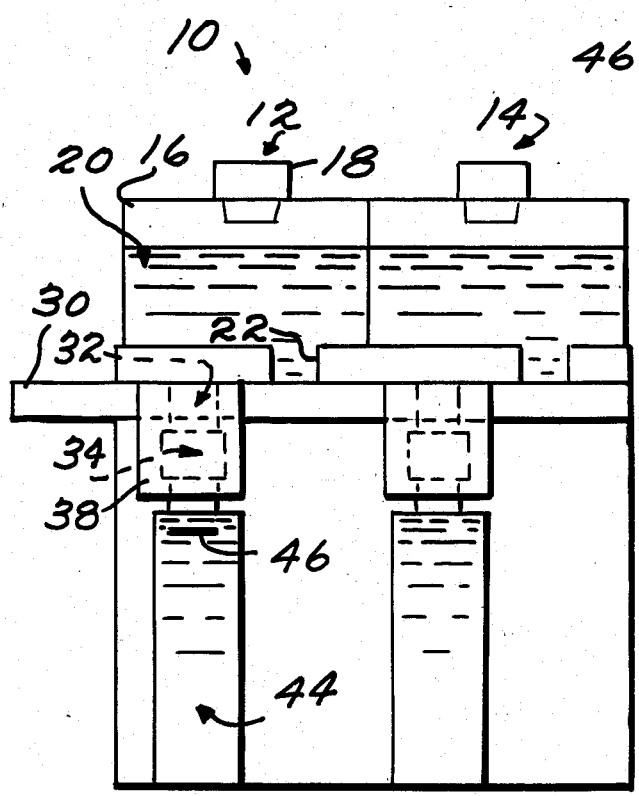

Slide 30 is pushed entirely to the left, as shown in FIG. 6c, to the mixing position. In this position measuring chamber 32 is disposed immediately above and in direct communication with passageway 34 which forms a portion of mixing chamber 44. Reagent contained in mixing chamber 32 thus drops into the sample of water contained in the mixing chamber. It should be observed that door 38 in this position completely covers and seals off exit port 36. This isolates the potentially harmful chemicals that may be contained within reagent 32 from exposure to the tester. Instrument 10 may thus be briefly shaken, using the extra air space in the upper portion of mixing chamber 44 to allow agitation of the mixture of reagent and water. This hastens mixture of the two and provides for quicker measurement results. The color of the reagent is then compared to the scales which are disposed adjacent to it (not shown in FIG. 6) to determine the test results.

With the test completed, the instrument is now readied for the next test. Instrument 10 is held in an upright position while slide 30 is returned to the loading position. Measuring chamber 32 carries atmospheric gas back to the loading position. This gas is exchanged with another measured amount of reagent when the loading position is reached. Doors 38 now uncover exit ports 36 so that the tested samples of water may be poured out of the mixing chambers and rinsed in preparation for the next test.

It can be seen that the test instrument provided by the present invention provides a very simplified testing apparatus. There are no check valves, one-way valves or springs which increase the cost of an instrument and provide increased opportunities for failure of operation. Gravitational forces are used to fill the measuring chamber with reagent and to dispense the reagent from the measuring chamber into the mixing chamber. There is thus no need for a plunger or other mechanism to force the reagent from a supply chamber into a mixing chamber. When slide 30 is in the loading position the instrument permits the introduction of a measured supply of sample water while at the same time measuring a predetermined volume of reagent corresponding to the water sample. By a single movement of the slide to the mixing position, the reagent is automatically introduced into the mixing chamber, the mixing chamber is sealed and the measuring chamber is replenished with a supply of atmospheric gas to automatically vent the reagent supply chamber during the next testing procedure. The reagent supply chamber is fully sealed from the exterior and from the tester. The preferred embodiment of the present invention further avoids the need for having rods or plungers extending through the reagent supply chamber, the mixing chamber, or both which creates additional sealing and operating problems.

While the invention has been particularly shown and described with reference to the foregoing preferred embodiment, it will be understood by those skilled in the art that other changes in form and detail may be made therein without departing from the spirit and scope of the invention. For instance, it would be possible to have supply chamber 20 and mixing chamber 44 disposed side-by-side so that slide 30 could capture a measured quantity of reagent from the side of supply chamber 20 and be shifted to a position along the side of mixing chamber 44 where the reagent could then be mixed with a water sample. Other such variations are also possible. It is therefore intended that the coverage afforded applicant be limited only by the claims and their equivalent language.

What is claimed is

1. A portable hand-held, pool-water test insrument for combining a predetermined volume of a reagent with a predetermined volume of water from a contained pool of water comprising:

means defining a supply chamber for providing a supply of reagent;

means defining a mixing chamber having a sampling port positioned to allow, when uncovered, water to flow into said mixing chamber when said instrument is held submerged in water, for holding a predetermined volume of water spaced from the supply chamber;

slide means containing a measuring chamber having a predetermined constant volume and which is shiftable between a loading position, where said measuring chamber is in communication with said supply chamber and is fillable with a predetermined volume of reagent from the supply of reagent and said mixing chamber is fillable with the predetermined volume of water, and a mixing position where said measuring chamber is in communication with said mixing chamber and the predetermined volume of reagent held in said measuring chamber is mixable with the predetermined volume of water held in said mixing chamber, said measuring chamber being positioned on said slide means so that it communicates with said supply chamber in said loading position and commuciates with said mixing chamber in said mixing position; and means joined to and shiftable with said slide means for uncovering said sampling port when said measuring chamber is in said loading position and for covering said sampling port when said measuring chamber is shifted to said mixing position.

2. The instrument of claim 1 further comprising means defining a second supply chamber for providing a supply of a second reagent;

means defining a second mixing chamber having a port position to allow, when uncovered, water to flow into said second mixing chamber when said instrument is held submerged in water, for holding a second predetermined volume of water spaced from the second supply chamber;

said slide means further containing a second measuring chamber having a second predetermined constant volume and which is shiftable between a loading position, where said second measuring chamber is in communication with said supply chamber and is fillable with a predetermined volume of reagent from the supply of second reagent and said second mixing chamber is fillable with the second predetermined volume of water, and a mixing position where said second mixing chamber is in communication with said second measuring chamber, and reagent held in said second measuring chamber is mixable with water held in said second mixing chamber, said second measuring chamber being positioned on said slide means so that it communicates with said second supply chamber in said loading position and communicates with said second mixing chamber in said mixing position; and second means joined to and shiftable with said slide means for uncovering said second sampling port when said second measuring chamber is in said loading position and for covering said second sampling port when said second measuring chamber is shifted to said mixing position.

3. The instrument of claim 1 wherein said slide means has upper and lower surfaces each having an opening communicating with said measuring chamber, said means defining a supply chamber further having a drain joining the bottom of said supply chamber with said upper surface opening when said slide means is in said loading position, and said mixing chamber having a passageway communicating with said lower surface opening when said slide means is in said mixing position.

4. The instrument of claim 3 wherein said measuring chamber has sides extending generally uniformly between said upper and lower openings and said drain and passageway are at least as large as said upper and lower openings, respectively.

5. The instrument of claim 3 wherein said measuring chamber is disposed directly below said drain when said slide means is in said loading position and is disposed directly above said passageway when said slide means is in said mixing position.

6. The instrument of claim 3 further including means defining a channel in which said slide means is matingly and slidably disposed, first sealing means interposed between said upper surface and said means defining a channel for sealing the junction between said drain and said upper surface opening from said means defining a channel when said slide is in said loading position and for sealing said upper surface opening from said drain when said slide is in said mixing position, and second sealing means interposed between said upper surface and said means defining a channel for sealing said upper surface opening from that portion of said means defining a channel generally extending beyond the path of said upper surface opening as it travels between said loading and mixing positions.

7. The instrument of claim 6 wherein said first sealing means includes a first O-ring disposed around the periphery of said upper surface opening and said drain and said second sealing means includes a second O-ring encircling said first O-ring and the travel path of said upper surface opening.

8. The instrument of claim 3 which further includes sealing means interposed between said lower surface and said means defining a channel defining means for sealing the passageway between said lower surface opening from said means defining a channel surrounding said lower surface opening.

9. The instrument of claim 8 wherein said sealing means includes an O-ring disposed around the periphery of said lower surface opening.

* * * * *